United States Patent [19]

Christensen et al.

[11] 4,350,631
[45] Sep. 21, 1982

[54] 6- AND 4-SUBSTITUTED-1-AZABICYCLO[3.2.0]HEPTAN-3,7-DIONE-2-CARBOXYLATES

[75] Inventors: Burton G. Christensen, Scotch Plains; David H. Shih, Manalapan, both of N.J.

[73] Assignee: Merck & Co., Inc., Rahway, N.J.

[21] Appl. No.: 245,005

[22] Filed: Mar. 18, 1981

Related U.S. Application Data

[63] Continuation-in-part of Ser. No. 217,931, Dec. 18, 1980, abandoned.

[51] Int. Cl.$^3$ ............................................. C09D 487/04
[52] U.S. Cl. ........................... 260/245.2 T; 260/239 A; 546/272
[58] Field of Search ................................. 260/245.2 T

[56] References Cited

U.S. PATENT DOCUMENTS

| | | | |
|---|---|---|---|
| 4,218,462 | 8/1980 | Christensen et al. | 260/245.2 T |
| 4,232,036 | 11/1980 | Christensen et al. | 260/245.2 T |
| 4,262,010 | 4/1981 | Christensen et al. | 260/245.2 T |
| 4,269,772 | 5/1981 | Melello et al. | 260/245.2 T |
| 4,273,709 | 6/1981 | Christensen et al. | 260/245.2 T |
| 4,282,148 | 8/1981 | Liu et al. | 260/245.2 T |
| 4,290,947 | 9/1981 | Christensen et al. | 260/245.2 T |
| 4,312,871 | 1/1982 | Christensen et al. | 260/245.2 T |

FOREIGN PATENT DOCUMENTS 7973 2/1980 European Pat. Off. .

OTHER PUBLICATIONS

Kametani et al., Heterocycles, vol. 14, pp. 1305–1308 (1980).

Primary Examiner—Mary C. Lee
Attorney, Agent, or Firm—James A. Arno; Hesna J. Pfeiffer

[57] ABSTRACT

Disclosed are 6- and 4-substituted-1-azabicyclo[3.2.0]heptan-3,7-dione-2-carboxylic acid esters and salts (I) which are useful in the preparation of 6-, 1- and 2-substituted carbapenem antibiotics.

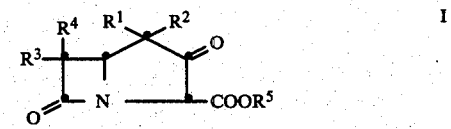

wherein $R^5$ is a pharmaceutically acceptable ester moiety or a removable protecting group or an alkali or alkaline earth metal cation such as sodium or potassium and wherein $R^1$, $R^2$, $R^3$ and $R^4$ are, inter alia, independently selected from the group consisting of hydrogen, alkyl, aryl and aralkyl.

7 Claims, No Drawings

6- AND 4-SUBSTITUTED-1-AZABICYCLO[3.2.0]HEPTAN-3,7-DIONE-2-CARBOXYLATES

BACKGROUND OF THE INVENTION

This application is a continuation-in-part of U.S. patent application Ser. No. 217,931 filed Dec. 18, 1980, now abandoned.

This invention relates to certain 6- and 4-substituted-1-azabicyclo[3.2.0]heptan-3,7-dione-2-carboxylates (I) which are useful in the preparation of 6-, 1- and 2-substituted carbapenam antibiotics (II):

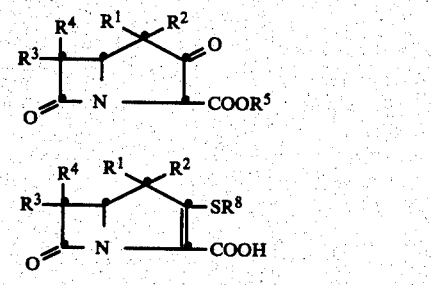

wherein $R^5$ is a salt cation such as sodium, potassium, or a removable carboxyl protecting group, or a pharmaceutically acceptable ester moiety; and wherein $R^1$, $R^2$, $R^3$, $R^4$ and $R^8$ are independently selected from the group consisting of hydrogen, substituted and unsubstituted: alkyl, alkenyl, and alkynyl, having from 1–10 carbon atoms; cycloalkyl, spirocycloalkyl, cycloalkylalyl, and alkylcycloalkyl, having 3–6 carbon atoms in the cycloalkyl ring and 1–6 carbon atoms in the alkyl moieties; aryl, such as phenyl; aralkyl, aralkenyl, and aralkynyl wherein the aryl moiety is phenyl and the alkyl has 1–6 carbon atoms; heteroaryl, heteroaralkyl, heterocyclyl and heterocyclylalkyl; wherein the substituent or substituents relative to the above-named radicals are selected from the group consisting of: amino, mono-, di- and trialkylamino, hydroxyl, alkoxyl, mercapto, alkylthio, arylthio such as phenylthio, sulfamoyl, amidino, guanidino, nitro, chloro, bromo, fluoro, cyano and carboxy; and wherein the hetero atom or atoms in the above-named heterocyclic moieties are selected from the group consisting of 1–4 oxygen, nitrogen or sulphur atoms; and wherein the alkyl moieties of the aboverecited substituents have 1–6 carbon atoms.

This invention also relates to the carboxyl derivatives of I which are antibiotics and which may be represented by the following generic structure (I):

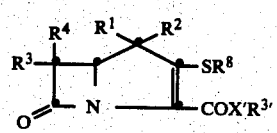

wherein X' is oxygen, sulphur or NR' (R'=H or lower alkyl having 1–6 carbon atoms); and $R^{3'}$ is, inter alia, representatively selected from the group consisting of hydrogen, conventional blocking groups such as trialkylsilyl, acyl and the pharmaceutically acceptable salt, ester and amide moieties known in the bicyclic β-lactam antiobitic art; the definition of $R^{3'}$ is given in greater detail below.

This invention also relates to processes for the preparation of such compounds I and II.

There is a continuing need for new antibiotics; and unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antiobiotics continues.

Thus, it is an objection of the present invention to provide antibiotics II, via intermediates I, which are useful in animal and human therapy and in inanimate systems. These antibiotics are active against a broad range of pathogens which representatively include both gram positive bacteria such as S. aureus, Strep. pyogenes, and B. subtilis, and gram negative bacteria such as E. coli, Pseudomonas, Proteus morganii, Serratia, and Klebsiella.

Such final products II are disclosed and claimed in the following co-pending, U.S. patents and U.S. patent applications.

1. U.S. Pat. No. 4,232,036.
2. U.S. patent application Ser. No. 99,275 filed Dec. 3, 1979, now U.S. Pat. No. 4,312,871.
3. U.S. patent application Ser. No. 99,288 filed Dec. 3, 1979 now U.S. Pat. No. 4,262,010.
4. U.S. Pat. No. 4,218,462.

To the extent that the aforementioned pending applications and issued patents define substituents $R^1$, $R^2$, $R^3$, $R^4$, and $R^5$ and to the extent that they representatively define $R^8$ and the utility of such final products II, they are hereby incorporated by reference.

DETAILED DESCRIPTION OF THE INVENTION

The process of the present invention may conveniently be summarized by the following reaction diagram:

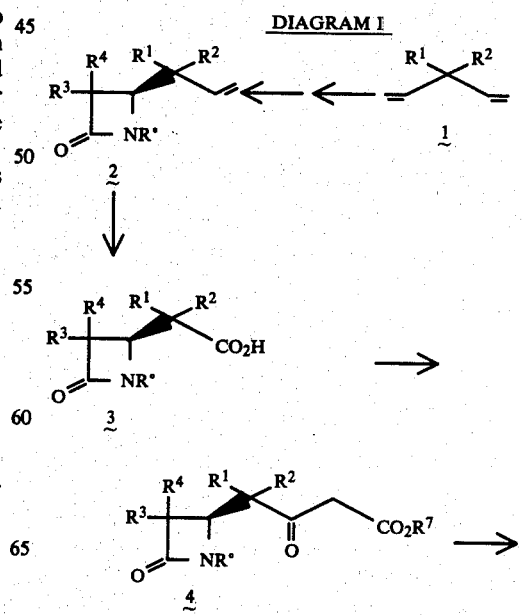

DIAGRAM I

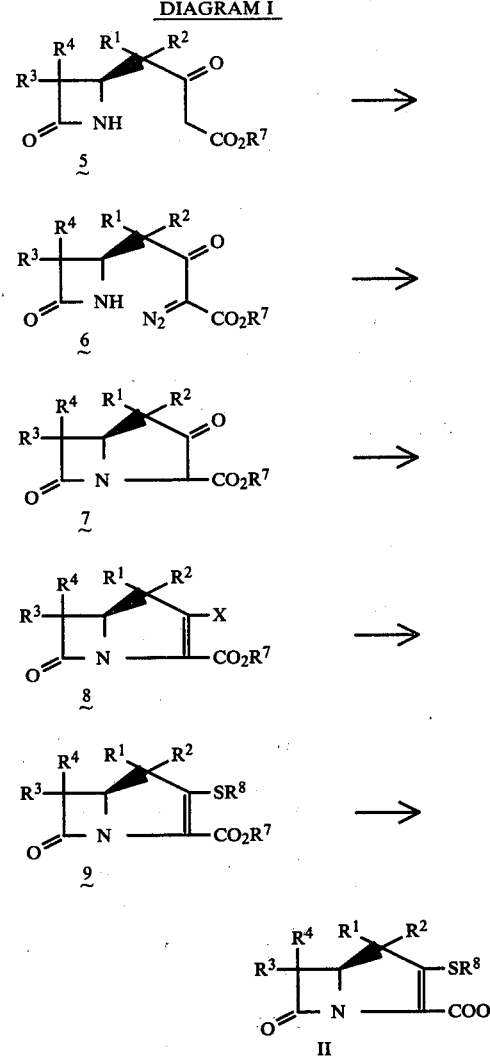

-continued
DIAGRAM I

In words relative to the diagram, the oxidation 2→3 is accomplished by treating 2 in a solvent such as methylenechloride, methanol, chloroform, or the like, with an oxidizing agent such as ozone, or the like, at a temperature of from −100° to 0° C. for from 0.1 to 4 hours, followed by treating the crude product with an oxidizing agent such as m-chloroperbenzoic acid, hydrogen peroxide, peracetic acid, or the like, at a temperature of from 0° C. to 100° C. for from 1 to 100 hours. R° is a readily removable protecting group and is defined below.

The addition 3→4 is accomplished by treating 3 with 1,1′-carbonyldiimidazole, or the like, in a solvent such as tetrahydrofuran, dimethoxyethane, acetonitrile or the like, at a temperature of from 0° to 70° C., followed by the addition of 1.1 to 3.0 equivalent of (R⁷O₂CCH₂CO₂)₂Mg, at a temperature of from 0° to 70° C. for from 1 to 48 hours. R⁷ is a pharmaceutically acceptable ester moiety or a readily removable carboxyl protecting groups such as p-nitrobenzyl, benzyl, or the like.

Removal of protecting group R° (4→5) (when R°=t-butyldimethylsilyl) is accomplished by acidic aqueous hydrolysis of 4 in a solvent such as methanol, ethanol, tetrahydrofuran, dioxane, or the like, in the presence of an acid such as hydrochloric, sulfuric, acetic or the like at a temperature of from 0° to 100° C. for from 2 to 18 hours.

The diazo species 6 is prepared from 5 by treating 5 in a solvent such as CH₃CN, CH₂Cl₂, THF, or the like with an azide such as p-carboxybenzenesulfonylazide, toluenesulfonylazide, methanesulfonylazide, or the like in the presence of a base such as triethylamine, pyridine, dimethylamine or the like for from 1 to 50 hours at 0°–50° C.

Cyclization (6→7) is accomplished by treating 6 in a solvent such as benzene, toluene, THF, cyclohexane, ethylacetate or the like at a temperature of from 25° to 110° C. for from 1–5 hours in the presence of a catalyst such as bis (acetylacetonato)Cu(II) [Cu(acac)₂], CuSO₄, Cu powder, Rh(OAc)₂ or Pd(OAc)₂. Alternatively, the cyclization may be accomplished by irradiating 6 through a pyrex filter (a wave length greater than 300 nm) in a solvent such as benzene, CCl₄, diethylether, or the like, at a temperature of from 0°–25° C. for from 0.5 to 2 hours. ["OAc"=acetate.]

Establishment of leaving group X (7→8) is accomplished by acylating the keto ester 7 with an acylating agent RX such as p-toluenesulfonic acid anhydride, p-nitrophenylsulfonic acid anhydride, 2,4,6-triisopropylphenylsulfonic acid anhydride, methanesulfonic acid anhydride, toluenesulfonyl chloride, p-bromophenylsulfonyl chloride, diphenylchlorophosphate, or the like; wherein X is the corresponding leaving group such as toluene sulfonyloxy, p-nitrophenylsulfonyloxy, methanesulfonyloxy, p-bromophenylsulfonyloxy and other leaving groups which are established by conventional procedures and which are well known in the art. Typically, the above acylation to establish leaving groups X is conducted in a solvent such as methylene chloride, acetonitrile or dimethylformamide, in the presence of a base such as diisopropylethylamine, triethylamine, 4-dimethylamino-pyridine or the like at a temperature of from −20° to 40° C. for from 0.5 to 5 hours. The leaving group X of intermediate 8 can also be halogen. The halogen leaving group is established by treating 7 with a halogenating agent such as φ₃PCl₂, φ₃PBr₂, (φO)₃PBr₂, oxalyl chloride, PBr₃ or the like in a solvent such as CH₂Cl₂, CH₃CN, THF, or the like in the presence of a base such as diisopropylethylamine, triethylamine, or 4-dimethylaminopyridine or the like. [φ=phenyl.]

The reaction 8→9 is accomplished by treating 8 in a solvent such as dioxane, dimethylformamide, dimethylsulfoxide, acetonitrile, hexamethylphosphoramide, or the like in the presence of an approximately equivalent to excess of the mercaptan reagent HSR⁸ wherein R⁸ as defined above. A representative mercaptan reagent is HSCH₂CH₂NHR⁸′ wherein R⁸′ is hydrogen or a readily removable N-protecting group such as p-nitrobenzyloxycarbonyl, o-nitrobenzyloxy carbonal, or the like in the presence of a base such as sodium hydrogen carbonate, potassium carbonate, triethylamine, diisopropylethylamine, or the like at a temperature of from −40° to 25° C. for from 1 to 72 hours. The mercaptan reagent, HSCH₂CH₂NHR⁸′, is typically prepared by treating aminoethylmercaptan in the presence of the desired acid chloride in the presence of a base such as sodium bicarbonate, sodium hydroxide, or the like in a solvent such as aqueous diethylether, aqueous dioxane, aqueous acetone, or the like at a temperature of from 0° to 25° C. for from 0.5 to 4 hours.

The final deblocking step 9→II is accomplished by conventional procedures such as hydrolysis or hydrogenation. Typically 9 in a solvent such as dioxane-water-ethanol, tetrahydrofuran-aqueous dipotassium hydrogen phosphate-isopropanol or the like is treated under a hydrogen pressure of from 1 to 4 atmospheres in the presence of a hydrogenation catalyst such as palladium on charcoal, palladium hydroxide, or the like at a temperature of from 0° to 50° C. for from 0.5 to 4 hours to provide II.

Relative to Diagram I, the following scheme is also employed in preparing mono-substituted intermediate material 3 (where $R^2=H$).

DIAGRAM II

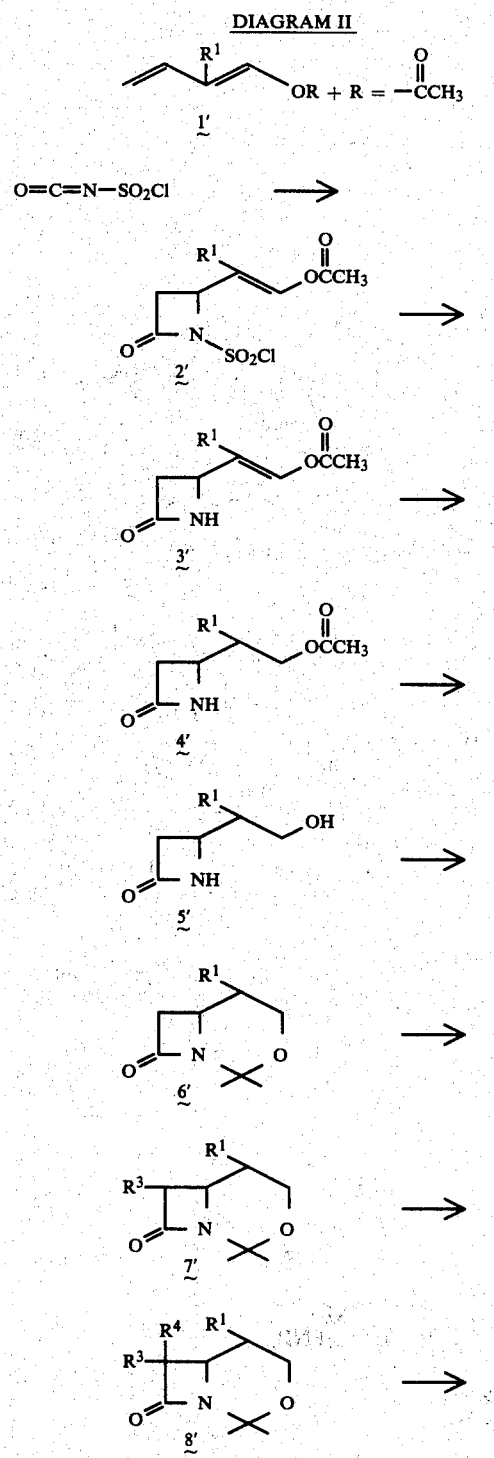

-continued
DIAGRAM II

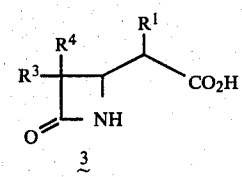

In words relative to the above diagram for the preparation of 3 (where $R^2=H$), the 4-(1-substituted-2-acetoxyvinyl)acetidinone-2-one (3') is prepared by reacting, for example ($R^1=CH_3$): chlorosulphonyl isocyanate and acyloxybutadiene (1') such as 1-acetoxy-2-methylbutadiene in a solvent such as anhydrous diethyl ether at a temperature of from about 31 30° C. to 0° C. under a nitrogen atmosphere. The reaction intermediate 2' is converted to 3' by hydrolysis. The reduction of 3' to provide 4-(1-methyl-2-acetoxyethyl)-2-azetidinone (4') is conducted by any convenient means such as hydrogenation in the presence of a catalyst such as platinum, palladium or oxides thereof under a hydrogen pressure of from 1 to 20 atmospheres in a solvent such as ethanol, ethylacetate, or the like at a temperature of from 0° to 25° C. for from 5 minutes to 1 hour. The 4-(2-hydroxy-1-methyl-ethyl)-2-azetidinone species 5' is obtained from 4' by hydrolysis. The 8-oxo-2,2,5-trimethyl-3-oxa-1-azabicyclo[4.2.0]octane species 6' is obtained on treatment of 5' with 2,2-dimethoxypropane in the presence of a catalyst such as boron trifluoride etherate in a solvent such as methylene chloride at a temperature of from 0° to 40° C. for from 1 to 40 minutes. Alkylation of 6' provides 7'. Typically, 6' is treated with a strong base such as lithium diisopropylamide, sodium hydride, phenyl lithium or butyl lithium and the like in a solvent such as tetrahydrofuran (THF), ether, dimethoxyethane, and the like at a temperature of from −80° to 0° C., whereupon the alkylating agent of choice, $R^6X$ is added ($R^6$ is as described above and X is chloro or bromo; alternatively, the alkylating agent may be $R^6$ tosylate, $R^6$-mesylate or an aldehyde or ketone such as acetaldehyde and the like) to provide mono-alkylated species 7'. When the desired dialkylated species 8' may be obtained from 7' by repeating the alkylating procedure, 6'→7'.

The conversion 8'→3 is obtained by oxidation. The most preferred oxidation is achieved by suspending 8' in a solvent such as acetone, benzene, hexane, or the like at a temperature of from 0° C. to 50° C. and treating with an oxidizing agent such as Jones reagent. Alternatively, compound 3 may be prepared from 8' by treating 8' with 50% trifluoroacetic acid/water at 0° to 50° C. for from 10 min. to 1 hr. to give the intermediate alcohol which is then oxidized with Jones reagent to 3.

The N-protecting group R° may be established on 3, as originally shown in Diagram I, by following the procedure 16→17, below; wherein R° is also defined.

Preparation of Starting Material 1 and 2

With respect to starting reagent 1, its preparation is generally described in *J. Amer. Chem. Soc.*, 74, 661 (1952) by E. B. Reid and T. E. Gompf, *J. Org. Chem.*, 23,1063 (1958) by R. Ciola and K. L. Burwell, Jr., and Belgium Patent 632,193 (1963) by R. Polster and E. Scharf. The following scheme summarizes the preparation of 1.

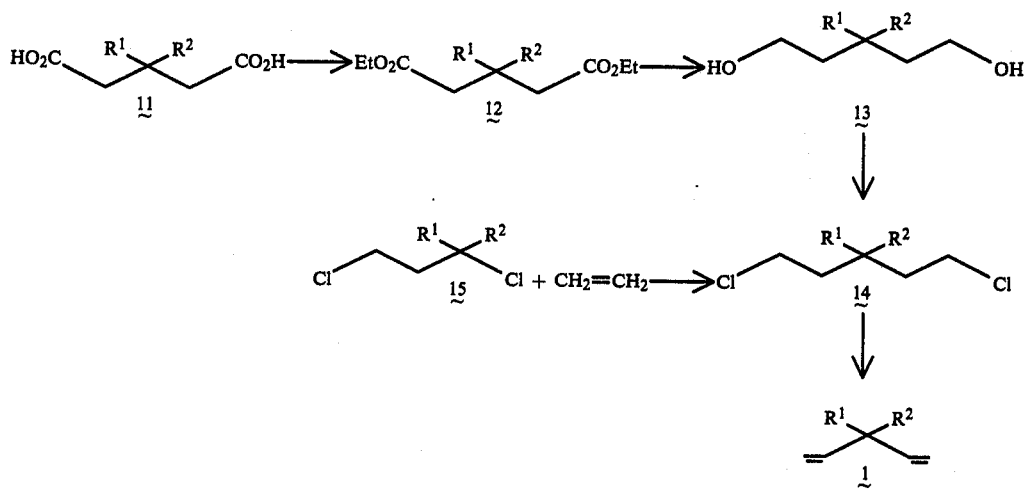

In words relative to the above scheme, the diester 12 is prepared by treating the diacid 11 with thionyl chloride at reflux for two hours followed by reacting with ethanol at 80° C. for 4 hours. Reduction of the diester 12 with lithium alumium hydride in ether at reflux for 4 hours followed by hydrolysis with 10% NaOH gives diol 13 which on further reaction with thionyl chloride gives dichloride 14. The dichloride 14 can be alternatively prepared by treating 15 with ethylene in the presence of alumium chloride. Treatment of the dichloride 14 with base such as 2-methylquinoline, DBU or sodium hydroxide in polyethylene glycol gives the expected 3-substituted 1,4-pentadiene 1.

Preparation of 2 is summarized in the following scheme:

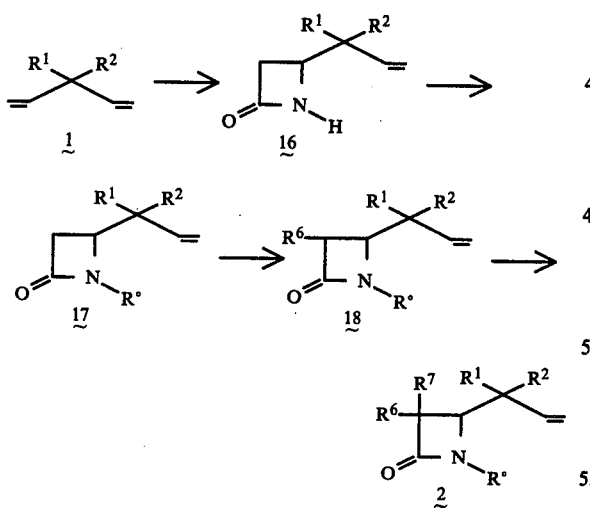

In words relative to above scheme, the substituted azetidinone 16 is prepared by reacting a 3-substituted 1,4-pentadiene 1 with chlorosulfonylisocyanate at 25° C. to 60° C. in a pressure bottle for 3–12 days, then the resulting mixture is hydrolyzed with aqueous sodium sulfite solution between pH 6.5–7.5 at 0° C. to 25° C. for from 5 min. to 60 min.

Azetidinone 16 is transformed (16→17) to establish the protecting group R° which may be a triorganosilyl group, such as t-butyldimethylsilyl, t-butyldiphenylsilyl, triphenylsilyl, isopropyldimethylsilyl, for example, or may be 3,4-dimethoxybenzyl, for example. Silyl protection is preferred, and typically R° is established by treating 16 in a solvent such as dimethylformamide, acetonitrile, hexamethylphosphoramide, tetrahydrofuran and the like with a silylating agent such as t-butyldimethylchlorosilane, t-butyldiphenylchlorosilane, triphenylchlorosilane, and the like at a temperature of from −20° C. to 25° C. for from 0.5 to 24 hours in the presence of a base such as triethylamine, diisopropylethylamine, or imidazole.

Alkylation of 17 provides 18. Typically, 17 is treated with a strong base such as lithium diisopropylamide, sodium hydride, phenyl lithium or butyl lithium and the like in a solvent such as tetrahydrofuran (THF), ether, dimethoxyethane and the like at a temperature of from −80° C. to 0° C., whereupon the alkylating agent of choice, $R^6X$ is added ($R^6$ is as described above and X is Iodo,chloro or bromo; alternatively the alkylating agent may be $R^6$-tosylate, $R^6$-mesylate or an aldehyde or ketone such as acetaldehyde and the like) to provide mono- alkylated species 18. When desired dialkylated species 2 may be obtained from 18 by repeating the alkylating procedure, 17→18.

In the foregoing description of the invention, suitable reagents $HSR^8$ (8→9) are representatively illustrated by the following list:
HSCH$_2$CH$_2$CH$_2$NHCO$_2$PNB,
PNBO$_2$CNHCH$_2$CH$_2$CH$_2$SX,

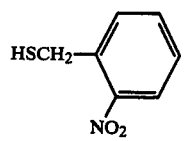

HSCH$_2$CH$_2$NHCO$_2$PNB
HSC(CH$_3$)$_2$CH$_2$NHCO$_2$PNB,
HSφ,
HSCH$_2$φ,
HSC(CH$_3$)$_3$,
HSCφ$_3$,

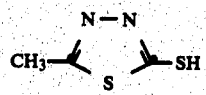

and the like (φ=phenyl; and PBN=p-nitrobenzyl),
CH$_3$SH,
CH$_3$CH$_2$SH,
CH$_3$(CH$_2$)$_2$SH,
(CH$_3$)$_2$CHSH,
CH$_3$(CH$_2$)$_3$SH,
(CH$_3$)$_2$CH(CH$_2$)$_2$SH,
CH$_2$=CHCH$_2$SH,
CH≡CCH$_2$SH,

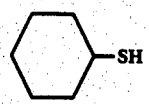

φ(CH$_2$)$_3$SH(φ=phenyl),
φ(CH$_2$)$_2$SH,
HO(CH$_2$)$_2$SH,
H$_2$N(CH$_2$)$_2$SH,
H$_2$N(CH$_2$)$_3$SH,
CH$_3$(CH$_2$)$_2$NH(CH$_2$)$_2$SH,

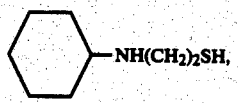

(CH$_3$)$_2$N(CH$_2$)$_2$SH,
(CH$_3$CH$_2$)$_2$N(CH$_2$)$_2$SH,
HO$_2$C(CH$_2$)$_2$SH,
φCH$_2$SH,

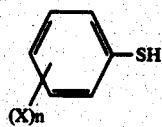

(n = 0, 1 or 2; X = Cl, Br, F, Cl, OCH$_3$, CH$_3$NH$_2$, NHCCH$_3$).

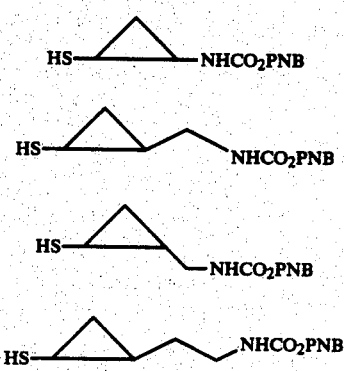

Similarly, suitable alkylating agents for establishing R$^6$ and/or R$^7$ at ultimate ring position 6 (17→18→2) are:
φCH$_2$CHO,
φCH$_2$CH$_2$CHO,
CH$_2$O,
CH$_3$I,
φCH Br,
CH$_3$COCH$_3$.

Relative to the compounds of the present invention I:

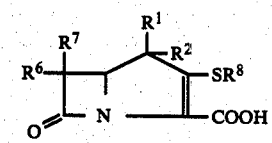

the most preferred values for R$^1$ and R$^2$ include:
ethyl,
propyl,
isopropyl,
cyclopropyl,
phenyl
benzyl
spiro-cyclopropyl The most preferred radicals for R$^6$ and R$^7$ are: R$^6$=H and R$^7$ is selected from hydroxymethyl, 1-hydroxyethyl, 1-hydroxypropyl, 2-hydroxypropyl, 2-hydroxyethyl; the most preferred values for R$^8$ are: aminoethylthio, aminopropylthio, aminocyclopropylthio, aminoisopropylthio, amidinoisopropylthio, and guanidinoethylthio.

The preferred esters used as protecting groups are those where R$^{3'}$ is benzyl, p-nitrobenzyl, o-nitrobenzyl, t-butyl, bromo-t-butyl, t-butyldimethylsilyl, trimethylsilyl, trichloroethyl; or R$^{3'}$ represents pharmaceutically acceptable ester moieties such as pivaloyloxymethyl, allyl, methallyl, (2-methylthio)-ethyl, 3-methyl-2-butenyl, p-t-butylbenzyl, 5-indanyl, 3-phthalidyl.

The final compounds II made available by the present invention are valuable antibiotics active against various gram-positive and gram-negative bacteria and, accordingly, find utility in human and veterinary medicine. Such sensitive bacteria representatively include: *Staphylococcus aureus, Escherichia coli, Klebsiella pneumoniae,* Serratia, *Salmonella typhosa,* Pseudomonas and *Bacterium proteus.* The resulting compounds may further be utilized as additives to animal feed, for preserving foodstuffs, and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example, in waterbased paints and in the white water of paper mills to inhibit the growth of harmful bacteria.

These antibiotics may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine;

lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, or syrups; or may be presented as a dry product, for reconstitution with water or other suitable vehicles before use. Such liquid preparations may contain conventional additives such as suspending agents, for example, sorbitol, syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid.

Compositions for injection may be presented in unit dose form in ampules, or in multidose container. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, or lotions.

Also, in addition to a carrier, the instant compositions may include other ingredients such as stabilizers, binders, antioxidants, preservatives, lubricators, suspending agents, viscosity agents or flavoring agents and the like. In addition, there may also be included in the compositions other active ingredients to provide a broader spectrum of antibiotic activity.

For veterinary medicine the composition may, for example, be formulated as an intramammary preparation in either long or quick-release bases.

The dosage to be administered depends to a large extent upon the general health and weight of the subject being treated, and the route and frequency of administration—the parenteral route being preferred for generalized infections and the oral route for intestinal infections. In general, a daily oral dosage consists of from about 2 to about 600 mg. of active ingredient per kg. of body weight of the subject in one or more applications per day. A preferred daily dosage for adult humans lies in the range of from about 15 to 150 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferably to employ a dosage amount in the range of from about 100 mg. to 1000 mg. In parenteral administration the unit dosage is usually the pure compound in a slightly acidified sterile water solution or in the form of a soluble powder intended for solution.

Especially preferred pharmaceutically acceptable salts and esters involving the carboxyl group of compounds of the present invention (I) are disclosed and claimed in co-pending U.S. patent application Ser. No. 861,314 (filed Dec. 16, 1977) now U.S. Pat. No. 4,181,733, which application is directed, inter alia, to pharmaceutically acceptable salts and esters of the carboxyl group of thienamycin. It is precisely these salts and esters which are preferred in the present invention and they are prepared in a manner analogous to that disclosed in U.S. patent application Ser. No. 861,314, now U.S. Pat. No. 4,181,733 which is incorporated herein by reference. Thus, especially preferred salts include sodium, potassium, ammonium, and the like; and especially preferred esters include pivaloxymethyl, p-t-butylbenzyl, 5-indanyl, 3-phthalidyl, 3-methyl-2-butenyl, and the like. One should note that when, in the total synthesis outlined above, $R^{3'}$ is a pharmaceutically acceptable ester moiety, there is no need for the final deblocking step if it is desired to have the final product I in the form of a pharmaceutically acceptable ester.

Especially preferred embodiments of the present invention are those, as defined above, except that any unsubstituted amino group borne on radical $R^8$ of Structure I is derivatized according to the teachings of Belgium Pat. No. 848,545 (issued May 20, 1977); the resulting amino group being represented thusly (partial structure):

$$\sim\sim N=C-X$$
$$\quad\quad\quad |$$
$$\quad\quad\quad Y$$

wherein X and Y are defined by the publication; species wherein X is H or lower alkyl and Y is $NH_2$ are especially preferred.

The following examples, illustrate but do not limit the product, process, compositional or method of treatment aspects of the present invention. All reaction temperatures are in °C.

EXAMPLE 1

Preparation of 3,3-Dimethyl-1,4-pentadiene

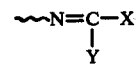      1

Procedure a $\beta,\beta$-Dimethylglutaric acid (obtained from Aldrich Chemical Company) (one mole), is refluxed for 2 hours with thionyl chloride (68% in excess). After removal of excess thionyl chloride, absolute ethanol (109% excess) is added slowly. The mixture is refluxed for 3 hours then distilled to collect the product, diethyl $\beta,\beta$-dimethylglutarate (98% yield).

To a suspension of lithium aluminum hydride (24 g) in ether (860 ml) is added dropwise with rapid stirring a solution of diethyl $\beta,\beta$-dimethylglutarate (124 g in 250 ml ether). The mixture is refluxed for 6 hours, then cooled to room temperature. Water (25 ml) is added slowly. The mixture is then titrated with 10% NaOH until a clear organic layer is obtained. The organic layer is separated, dried over anhydrous sodium sulfate then evaporated in vacuo to give the resulting diol as an oil (90% yield), b.p.95° at 1.0 mm. The 3,3-dimethyl-1,5- pentanediol (0.5 mole) is treated with thionyl chloride (1.05 mole) at reflux for 3 hours. After removal of excess thionyl chloride in vacuo, the 3,3-dimethyl-1,5-dichloropentane is obtained (90% yield).

3,3-Dimethyl-1,5-dichloropentane (41 g) is added dropwise at 170° C. to a mixture of 48 g of sodium hydroxide and 40 g of polyethylene glycol tetramer and the mixture is distilled to give 3,3-dimethyl-1,4-pentadiene (66%).

Procedure b

At −40° C., 1,3-dichloro-3-methylbutane (50 g) is mixed with alumium chloride (5 g). The ethylene is bubbled through the mixture for 4 hours. The mixture is allowed to warm to room temperature and hydrolyzed with water. The mixture is extracted with ethyl acetate to give 3,3-dimethyl-1,5-dichloropentane.

A mixture of 0.5 mole of 3,3-dimethyl-1,5-dichloropentane, 2-methylquinoline (2 moles), and sodium iodide (0.1 mole) is refluxed in a flask equipped with a Vigreaux column at the top of which is a condenser and take-off. The diolefin 1 is collected during 8 hrs reaction. The product is dried over anhydrous sodium sulfate.

EXAMPLE 2

Preparation of 3-methyl-1,4-pentadiene

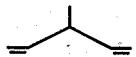

2

Following the procedure of Example 1(a), but replacing β,β-dimethylglutaric acid with an equivalent amount of β-methylglutaric acid, 3-methyl-1,4-pentadiene is obtained.

EXAMPLE 3

Preparation of 4-(1,1-dimethyl-pro-2-enyl)azetidin-2-one

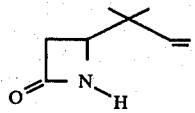

3

In a sealed tube, 3,3-dimethyl-1,4-pentadiene (9.6 g) and chlorosulfonyl isocyanate (14.2 g) are allowed to stand at room temperature for 6 days. The resulting mixture is diluted with methylene chloride and added slowly to a stirred aqeous solution which contains 20 g of Na₂SO₃ and 50 g of K₂HPO₄ at 0°–5° C. for 30 min. The organic layer is separated and dried over Mg₂SO₄. After evaporation, the crude product is chromatographed on silica gel GF eluting with EtOAc to give 3.

EXAMPLE 4

Preparation of 4-(1-methyl-pro-2-enyl)azetidin-2-one

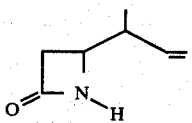

4

Following the procedure of Example 3, but replacing 3,3-dimethyl-1,4-pentadiene with 3-methyl-1,4-pentadiene, the title compound 4 is obtained.

EXAMPLE 5

Preparation of 5

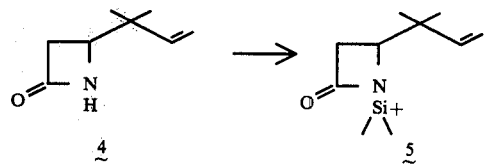

t-Butyldimethylchlorosilane (7.51 g) is added in one portion to an ice-cold, stirred solution of 4-(1,1-dimethyl-prop-2-ene)-azetidin-2-one (6.54 g) and triethylamine (12 ml) in anhydrous dimethylformamide (100 ml). The reaction mixture is stirred at 0°–5° C. for 1 hour and then allowed to warm to room temperature. Most of the solvent is removed under vacuum to give a residue which is partitioned between diethyl ether (250 ml) and water. The ethereal phase is washed with 2.5 N hydrochloric acid (50 ml), water (3×50 ml), and brine, dried with magnesium sulfate, filtered and evaporated under vacuum to provide a crude product which is purified by chromatography on silica gel (20% ether in petroleum ether) to yield 5.

EXAMPLE 6

Preparation of 6

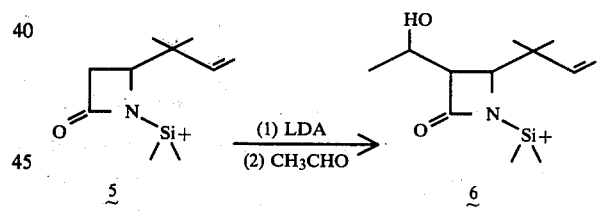

n-Butyllithium in hexane (26.25 mmol) is added slowly by syringe to a solution of diisopropylamine (26.25 mmol) in anhydrous tetrahydrofuran (100 ml) at −78° C. The resulting solution is stirred for 15 min. prior to the addition of a solution of 5 (25.0 mmol) in anhydrous tetrahydrofuran (25 ml). After stirring for 15 min. at −78° C., acetaldehyde (75 mmol) is added by syringe and the resulting solution is stirred at −78° C. for 5 min. Saturated aqueous ammonium chloride solution (15 ml) is added by syringe and the reaction mixture is allowed to warm to room temperature, then diluted with ether (250 ml) and washed with 2.5 N hydrochloric acid solution (2×50 ml), water (100 ml) and brine and dried over magnesium sulfate. Solvents are removed in vacuo and the residue is chromatographed on silica gel (1:1, ether:petroleum ether) to give the expected product 6.

EXAMPLE 7

Preparation of 7

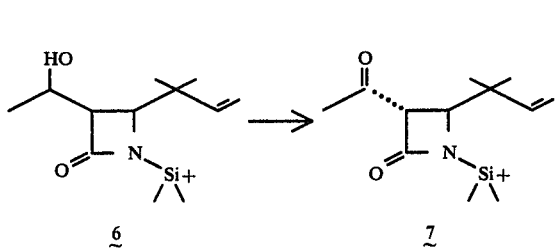

A. Trifluoroacetic anhydride (7.5 mmol) is added dropwise by syringe to a solution of dimethylsulfoxide (10 mmol) in anhydrous methylene chloride (15 ml) at −78° C. The resulting mixture is stirred at −78° C. for 20 min. A solution of 6

(5.0 mmol) in methylene chloride (15 ml) is added by syringe and the cooling bath is removed. After an additional 1 hr., the reaction mixture is diluted with methylene chloride (100 ml), washed with water (50 ml) and brine and dried over magnesium sulfate. Removal of solvents in vacuo yields crude product which is chromatographed on silica gel (2:1, petroleum ether:ether) to yield 7.

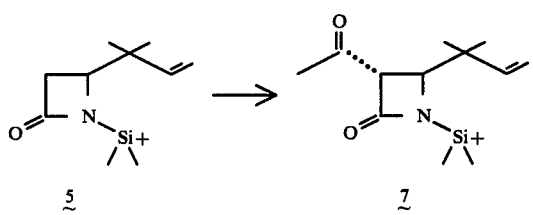

B. n-Butyllithium in hexane (4.10 mmol) is added by syringe to a solution of diisopropylamine (4.10 mmol) in anhydrous tetrahydrofuran (16 ml) at −78° C. The resulting solution is stirred at −78° C. for 15 min. prior to the addition of a solution of 1-(t-butyldimethylsilyl)-4-(1,1-dimethyl-prop-2-enyl)-azetidin-2-one 5 (2.0 mmol) in anhydrous tetrahydrofuran (2 ml). After an additional 15 min. at −78° C., the reaction mixture is added via a Teflon tube to a mixture of N-acetylimidazole (4.1 mmol) in anhydrous tetrahydrofuran (16 ml) at −78° C. The resulting yellow reaction mixture is stirred at −78° C. for 15 min., then quenched by addition of saturated aqueous ammonium chloride solution (10 ml). The reaction mixture is diluted with ether (100 ml) and washed with 2.5 N hydrochloric acid solution (25 ml) water (25 ml) and brine. The organic phase is dried over magnesium sulfate and concentrated in vacuo to yield a crude product. This material is chromatographed on silica gel (2:1 petroleum ether:ether) to yield 7.

EXAMPLE 8

Preparation of 6

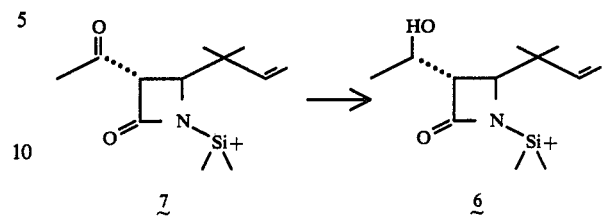

K-Selectride (potassium tri-(sec)-butylborohydride) in tetrahydrofuran (4.8 mmol) is added by syringe to a mixture of potassium iodide (2.0 mmol) and 7 (2.0 mmol) in anhydrous ether (20 ml) at room temperature. The resulting mixture is stirred at room temperature for 2.5 hours, then quenched by addition of glacial acetic acid (9.6 mmol). The resulting mixture is diluted with ethylacetate (100 ml) and filtered through celite. Removal of solvents in vacuo gives crude product which is chromatographed on silica gel (1:1 ether:petroleum ether) to yield 1.90 g (95%) of 6.

EXAMPLE 9

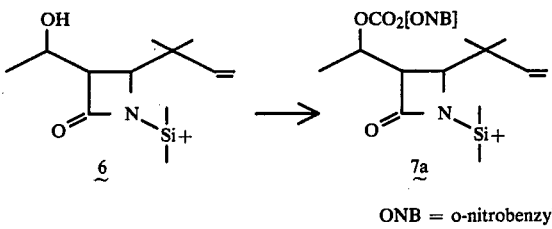

ONB = o-nitrobenzyl

Under anhydrous conditions at 0° C. a solution of 6 (3.50 g) in 60 ml methylene chloride is treated with 4-dimethylaminopyridine (3.32 g) and o-nitrobenzylchloroformate (5.88 g). The mixture is allowed to warm to room temperature and stirred for 1 hr. The resulting mixture is washed with 0.1 N HCl, water, brine and water. The organic layer is separated, dried over $Na_2SO_4$ and allowed to evaporate in vacuo to give crude products. The crude products, dissolved in 20 ml ether and chilled at −5° C., give the o-nitrobenzyl alcohol (0.5 g) which is separated by filtration. Purification by HPLC (silica gel) eluting with 40% ethylacetate/cyclohexane to gives 7a.

EXAMPLE 10

Preparation of 8.

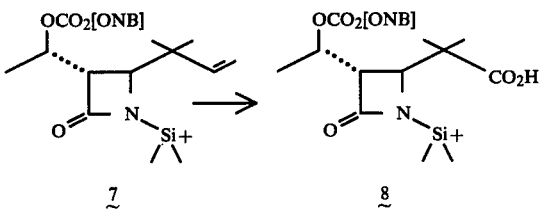

A solution of 7 (3.0 mmol) in dry methylene chloride (30 ml) is cooled to −78° C. (dry ice-acetone) and a stream of ozone is bubbled through until the reaction mixture becomes blue. The ozone flow is then stopped and the reaction is purged by bubbling through nitrogen until the blue color disappears. Solid m-chloroperbenzoic acid (3.0 mmol) is added and the cold bath is removed. When the reaction mixture reaches room temperature, the flask is fitted with a reflux condenser and the mixture is heated at reflux for three days. Removal of solvents in vacuo gives crude product which is chromatographed on silica gel (2% glacial acetic acid in methylene chloride) to 8.

EXAMPLE 10a

Preparation of 8a

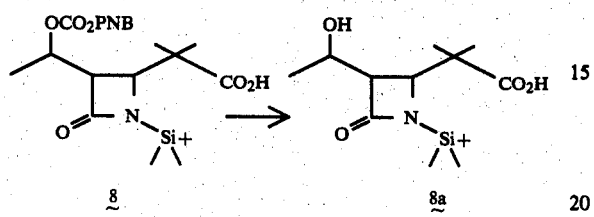

The acid 8 (1.0 mmol) is hydrogenated in 30 ml ethyl acetate under 1 atm H₂ in the presence of 0.1 mmol of 10% Pd/C at room temperature for 30 min. The mixture is filtered from catalyst. The filtrate is evaporated in vacuo to give 8a.

EXAMPLE 11

Preparation of 9.

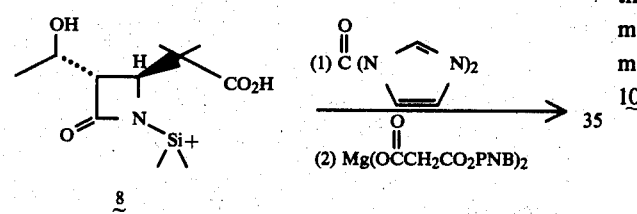

1,1'-Carbonyldiimidazole (1.10 mmol) is added in one portion to a solution of 8 (1.0 mmol) in anhydrous tetrahydrofuran (5 ml) at room temperature. The resulting solution is stirred at room temperature for 6 hours. In a second flask, magnesium ethoxide (5 mmol) is added in one portion to a solution of the mono-p-nitrobenzyl ester of malonic acid (10 mmol) in anhydrous tetrahydrofuran (25 ml). The resulting mixture is stirred at room temperature for 1 hr., then the tetrahydrofuran is removed at the pump and the residue is triturated with ether to yield the magnesium salt. This magnesium salt is then added to the first reaction flask and the resulting mixture is stirred at room temperature for 18 hrs. The reaction mixture is then poured into 50 ml of ether, washed with 0.5 N hydrochloric acid solution (20 ml), water (20 ml), saturated aqueous sodium bicarbonate solution (20 ml), brine and dried over magnesium sulfate. Removal of solvents in vacuo gives crude product which is chromatographed on silica gel (ether) to yield 9.

EXAMPLE 12

Preparation of 10.

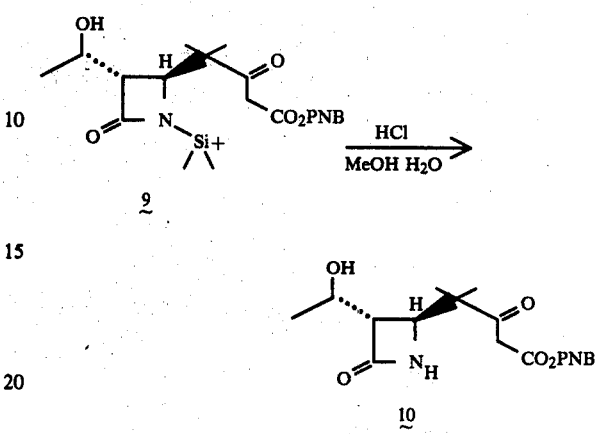

A solution of 9 (1.0 mmol) in 20 ml of 9:1 (v/v) methanol-water is cooled to 0° C. Concentrated hydrochloric acid (0.34 ml) is added and the resulting solution is stirred at 0° C. for 15 min., then allowed to warm to room temperature. After 2.5 hrs., at room temperature the reaction mixture is diluted with ethyl acetate (25 ml), washed with water (10 ml) and brine, dried over magnesium sulfate and concentrated in vacuo to yield 10.

EXAMPLE 13

Preparation of 11

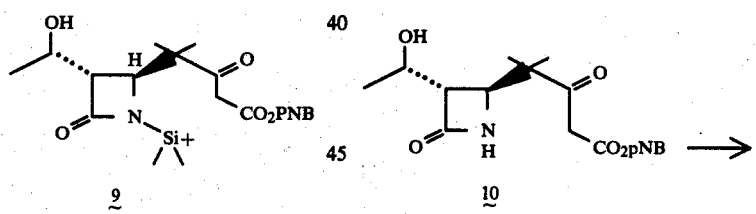

Triethylamine (263 mg) is added by syringe to a mixture of 10 (253 mg) and p-toluenesulfonylazide (196 mg) in dry acetonitrile (6 ml) at 0° C. When addition is complete the cooling bath is removed and the reaction mixture is stirred at room temperature for 1 hour. The mixture is then diluted with ethyl acetate (50 ml) and filtered. The filtrate is concentrated in vacuo and the residue is chromatographed on a short silica gel column (ethyl acetate) to yield 11.

EXAMPLE 14

Preparation of 12

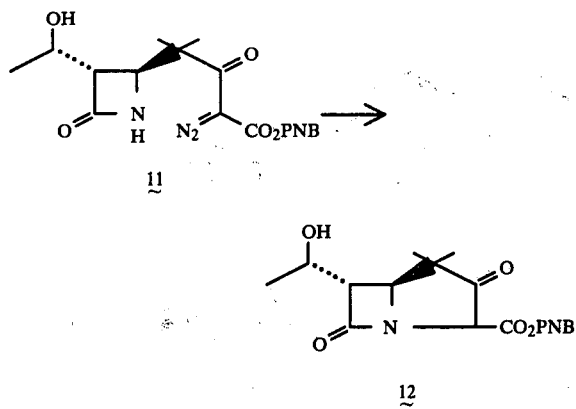

A suspension of 11 (56.4 mg) and rhodium (II) acetate (0.1 mg) in cyclohexane (3 ml) is deoxygenated by bubbling through nitrogen for 10 minutes. The mixture is then heated to 78° C. for 1 hour. During heating the solid starting material gradually goes into solution. The mixture is then cooled, filtered to remove the catalyst, and the filtrate is concentrated in vacuo to yield 12.

EXAMPLE 15

Preparation of p-Nitrobenzyloxycarbonylaminoethanethiol

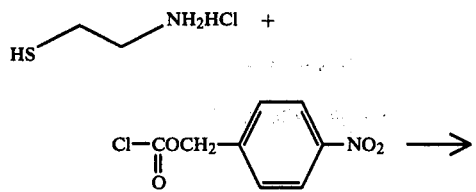

To 600 ml diethyl ether (Et$_2$O)-75 ml H$_2$O in an ice bath with stirring is added 3.2 g cysteamine hydrochloride (mw=114; 28.1 mmole). A solution of 7.14 g NaHCO$_3$ (mw=84; 85 mmole) in 75 ml H$_2$O is added. The ice bath is removed, and at room temperature a solution of 6.75 g p-nitrobenzylchloroformate (mw=216; 31.3 mmole) in 270 ml Et$_2$O is added dropwise over a period of one hour. After 10 additional minutes, the layers are separated. The ether layer is extracted with 150 ml 0.25 N HCl, and then with 200 ml brine. Each aqueous layer is then backwashed successively with 100 ml Et$_2$O. The combined Et$_2$O layers are dried over anhydrous MgSO$_4$, filtered, and concentrated under a N$_2$ stream. The crystalline residue is slurried in a small amount of ether, filtered, and the pale yellow crystals are dried under high vacuum to give 4.7 g. p-nitrobenzyloxycarbonylaminoethanethiol (65% yield). NMR (CDCl$_3$): 8.18 (d, J=8 Hz, aromatic protons ortho to nitro), 7.47 (d, J=8 Hz, aromatic protons meta to nitro), 5.27 (—NH—), 5.20 (s, CH$_2$—NH—), 2.67 (m, —CH$_2$—SH), 1.35 (t, J=8.5 Hz, —SH) in ppm downfield from TMS. IR (CHCl$_3$) solution): carbonyl-1725 cm$^{-1}$. M.S.: molecular ion-256, (M-47) at 209, (M-136) at 120, +CH$_2\phi$pNO$_2$ at 136.

EXAMPLE 15a

Following the procedures of Example 15, N-p-nitrobenzyloxycarbonylaminocyclopropylthio is obtained when an equivalent amount of aminocyclopropylthiol hydrochloride is substituted for the cysteamine hydrochloride of Example 15.

EXAMPLE 16

Preparation of 13

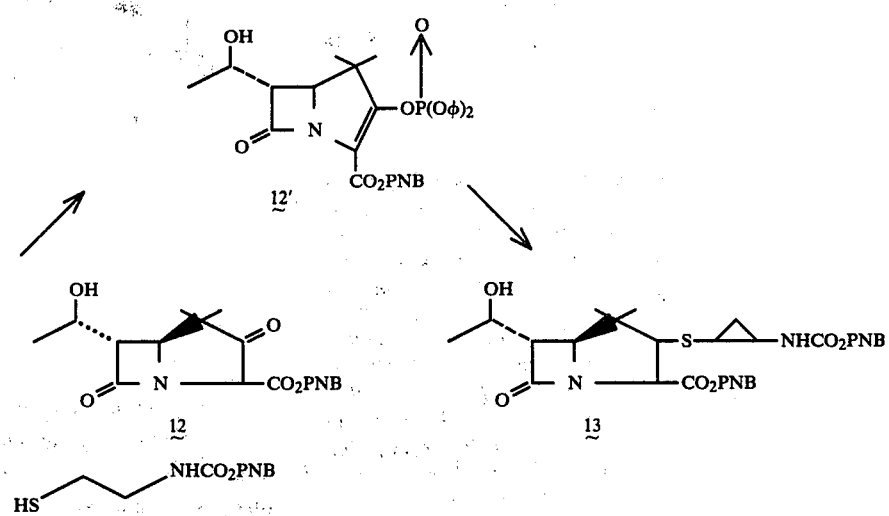

The starting material 12 (51 mg) is dissolved in acetonitrile (3 ml) and the resulting solution is cooled to 0° C. Diisopropylethylamine (22 mg) is added by syringe and the resulting solution is stirred at 0° C. for 1 minute prior to the addition of a solution of diphenylchlorophosphate (51 mg) in dry acetonitrile (1 ml). The resulting solution is stirred at 0° C. for 1 hour to provide intermediate 12, then cooled to −25° C. Diisopropylethylamine (80.5 mg) is added by syringe followed shortly thereafter by a solution of N-p-nitrobenzyloxycarbonylaminocyclopropylthiol (40 mg) in 1 ml of dry acetonitrile. The reaction mixture is then stored in a refrigerator for 70 hr. The mixture is diluted with 25 ml of ethyl acetate washed with brine and dried over magnesium sulfate. Solvents are removed in vacuo to yield crude product which is chromatographed on a silica gel plate to yield 13.

EXAMPLE 17

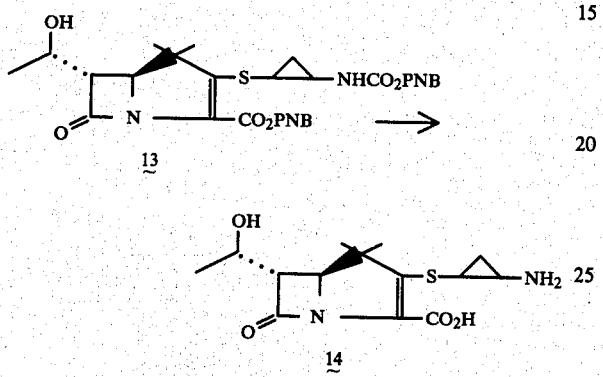

A mixture of 13 (10 mg) and 10% Pd/C-Bolhofer type in tetrahydrofuran (2 ml), 0.1 M dipotassium hydrogen phosphate solution (1.4 ml) and 2-propanol (0.2 ml) is hydrogenated at 40 psi on the Parr shaker for 30 minutes. The mixture is then filtered and the catalyst is washed with water. The combined filtrate and washings are extracted with ethyl acetate-ethyl ether then concentrated to ~3 ml and lyophilized to give 14.

EXAMPLE 18

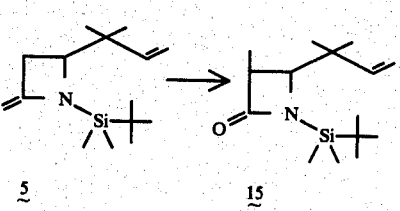

THF, 20 ml, is placed under N₂, treated with 1.54 ml diisopropylamine and cooled to −78° C. A solution of n-butyl lithium 1.97 M in hexane (5.6 ml) is added dropwise over 5 min. The reaction mixture is stirred at −78° C. for 10 min. and then treated with 5 (2.14 g) in 15 ml THF which is added dropwise over 5 min. After another 10 min. hexamethylphosphoramide (1.97 ml) is added. The mixture is stirred another 10 min., then treated with 2 ml of methyl iodide. The reaction mixture is stirred at −78° C. for 15 min. and allowed to warm to 25° C. and stirred for 15 min. The reaction mixture is diluted with EtOAc, washed once with pH 7 phosphate buffer then dried and evaporated. The residue is chromatographed on silica gel using 25% EtOAc/C₆H₆ as eluant to give 15.

EXAMPLE 19

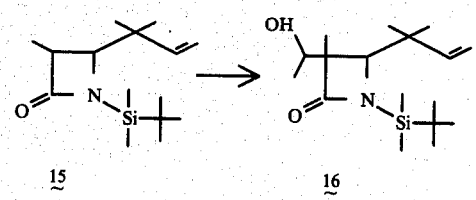

To a solution of 1.1 equivalents of freshly prepared lithium diisopropylamide in anhydrous tetrahydrofuran under a nitrogen atmosphere at −78° C. is added a solution of 15 in anhydrous tetrahydrofuran which has been cooled to −78° C. After two minutes, the resulting lithium enolate is treated with 3 equivalents of acetaldehyde. The solution is stirred for 30 minutes at −78° and then poured into water. The aqueous phase is saturated with sodium chloride and extracted with ethyl acetate. The combined ethyl acetate solutions are dried over magnesium sulfate and filtered. The filtrate is evaporated under reduced pressure to give the crude product. Purification by chromatography on silica gel using ethyl acetate/benzene gives 16.

EXAMPLE 20

Preparation of 18

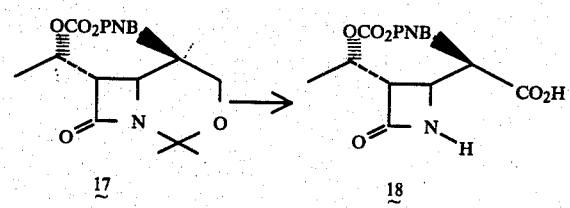

The bicyclic azetidinone (6.0 g) suspended in acetone (60 ml) at 0° C. is treated with 4 N Jones reagent (9.4 ml). The mixture becomes homogenous upon the treatment of Jones reagent. After stirring at 0° C. for 30 min., some white ppts forms. After 50 min, the reaction is quenched with isopropanol (1.0 ml) for 10 min. The white ppts is collected by filtration and washed with water and acetone to give 3.2 g of product. The filtrate is extracted with EtOAc (200 ml) to give additional 1.2 g of product.

EXAMPLE 21

Preparation of 19

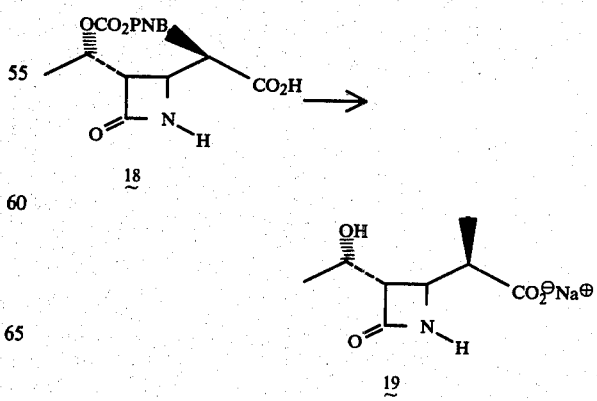

The azetidinone carboxylic acid (0.37 g) is suspended in 5 ml water. The mixture is adjusted and maintained at pH 12.0 with 2.5 N NaOH with constant stirring at room temperature for 30 min. The mixture is then neutralized with 2.5 N HCl to pH 7.5, and extracted with 5 ml EtOAc. The aqueous layer is separated, concentrated and lyophilized to give white solid product 19. NMR (60 MHz, D$_2$O): δ1.06 (d), 1.25(d), 2.40 (m), 3.02(q), 3.56(q), 4.05(m).

EXAMPLE 22

Preparation of 20

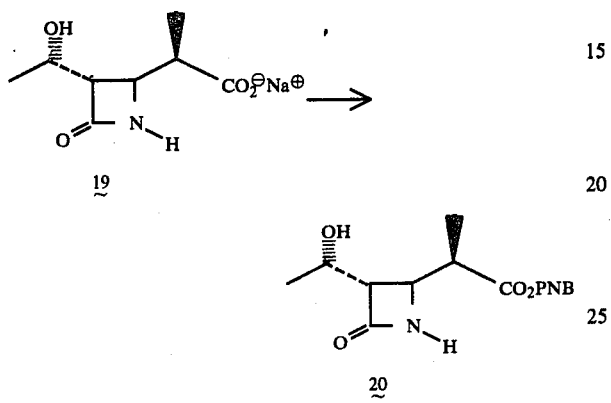

The sodium salt of azetidinone carboxylic acid 19 (0.45 g) and p-nitrobenzylbromide (0.43 g) in DMF (6 ml) are stirred under nitrogen atmosphere at room temperature for 2 hrs. The resulting homogenous solution is evaporated in vacuo to give crude product which is purified by silica gel column eluted first with 10% EtOAc/cyclohexane. The desirable fractions are combined, concentrated and evaporated in vacuo to give product 20(0.37 g). IR (neat): 1760 cm$^{-1}$; NMR (60 MHz, CDCl$_3$): δ1.30(d), 2.63(m), 3.03(q), 3.75(q), 4.03(m), 5.21(s), 6.41(broad singlet), 7.48(d) and 8.20(d).

EXAMPLE 23

Preparation of 21

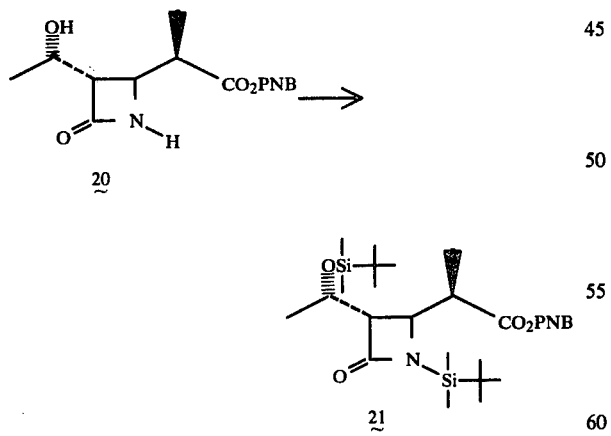

The azetidinone p-nitrobenzyl ester 20 (2.83 g) is stirred with t-butyldimethylchlorosilane (3.98 g) and triethylamine (7.35 ml) in DMF (26 ml) under nitrogen atmosphere at room temperature for 5 hrs. The mixture is filtered from precipitates and the filtrate is evaporated in vacuo to give crude product. HPLC purification of the product (Porasil, 30% ethyl acetate/cyclohexane solvent system) affords 21 (4.2 g) after evaporation of solvent. NMR (60 MHz, CDCl$_3$): δ0.01 (s), 0.10(s), 0.85(s), 0.90(s), 1.09(d), 1.21(d), 2.98(m), 3.42(q), 3.64(q), 4.08(m), 5.20(s), 7.50(d), and 8.23(d).

EXAMPLE 24

Preparation of 22

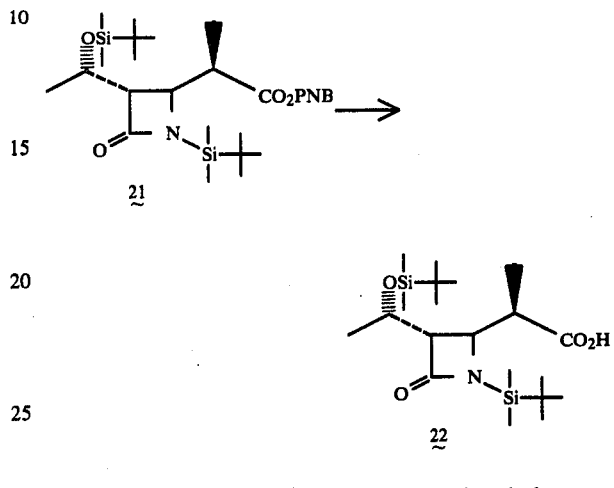

The azetidinone 21 (2.1 g) is dissolved in ethylacetate (40 ml) and hydrogenated under 50 psi of hydrogen in the presence of 10% Pd/C (0.4 g) for 30 min. The mixture is filtered through super-cell, and the filtrate is diluted with 100 ml EtOAc and washed with 0.1 N HCl (100 ml) and brine. The organic layer is separated, dried over anhydrous sodium sulfate, and evaporated in vacuo to give product 22 (1.45 g), NMR (CDCl$_3$): δ0.01(s), 0.16(s), 0.82(s), 0.90(s), 1.11(d), 1.22(d), 2.90–3.05(m), 3.40(q), 3.62(q) and 3.80–4.40 (m).

EXAMPLE 25

Preparation of 23

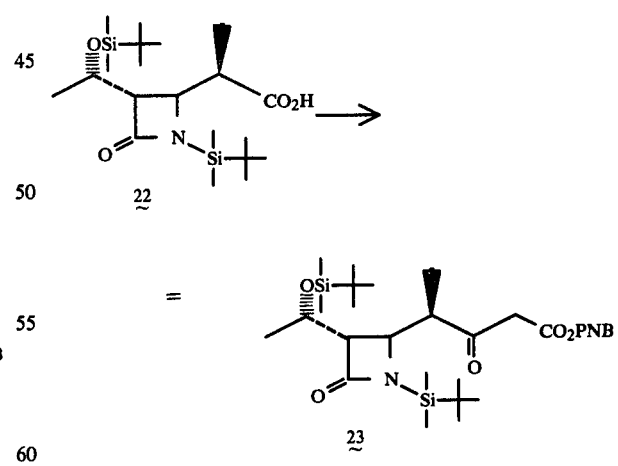

Under nitrogen atmosphere the suspension of the diprotected azetidinone 22 (1.04 g) in acetonitrile (20 ml) is treated with carbonyldiimidazole (0.51 g) at room temperature for 2 hrs. The resulting homogenous solution is mixed with p-nitrobenzylmalonate magnesium salt (1.57 g) and stirred at 60° C. for 5 hrs. The mixture is filtered, evaporated and chromatographed on silica gel plates eluting with 40% EtOAc/cyclohexane to give product 22 (0.83 g). IR (Neat): 1748 cm$^{-1}$; NMR (60 MHz, CDCl$_3$): 0.02 (s), 0.20(s), 0.85(s), 0.95(s), 1.19(d), 1.22(d), 2.80–3.20 (m), 3.58(s), 3.50–4.20(m), 5.23(s), 7.45(d) and 8.17(d).

EXAMPLE 26

Preparation of 24

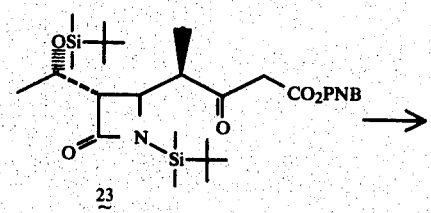

23

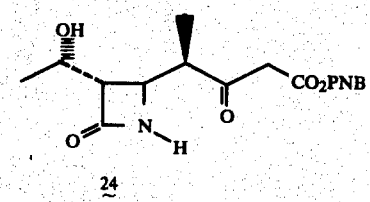

24

The disilyl azetidinone 23 (55 mg) dissolved in methanol (1 ml) is treated with 0.1 N HCl (0.2 ml) at room temperature for 3 hrs. The mixture is evaporated in vacuo to give oil residue which is taken up in ethylacetate. After the mixture is washed with brine, the organic layer is separated, dried over anhydrous sodium sulfate. The crude product is chromatographed by silica gel plates eluting with ethyl acetate to give product 24 (11.8 mg). IR (Neat); 1748 cm$^{-1}$; NMR (CDCl$_3$): δ1.23(d), 1.50(d), 2.50–3.30(m), 3.72(s), 3.60–4.40(m), 5.30(s), 6.35(broad singlet), 7.50(d) and 8.26(d).

EXAMPLE 27

Preparation of 25

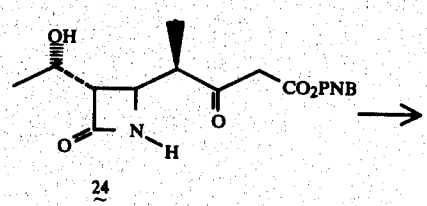

24

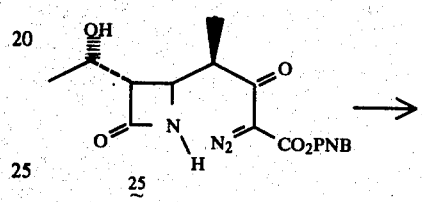

25

Following the procedure of Example 13, except making the indicated substitution, there is obtained product 25: IR (Neat): δ2150 (N$_3$), 1754 and 1715 cm$^{-1}$; NMR (CDCl$_3$): δ1.20(d), 1.31(d), 2.60–3.20(m), 3.60–4.40(m), 5.35(s), 7.50(d) and 8.20(d).

EXAMPLE 28

Preparation of 26

25

26

A 10-ml, two necked round-bottomed flask is equipped with a reflux condenser and a nitrogen inlet tube. To the flask is added diazo azetidinone 1 (110 mg), rhodium acetate (0.2 mg) and ethyl acetate (3 ml). The mixture is heated at reflux for 10 min, then cooled to room temperature and washed with 0.5 ml water. The organic layer is separated, dried over anhydrous magnesium sulfate then evaporated in vacuo to give product 26, IR(neat): 1764 cm$^{-1}$ (β-lactam); NMR (60 MHz, CDCl$_3$): δ1.18(d), 1.35(d), 2.77(quintets) 3.30(q, J=3.0 and 6.0 Hz), 4.17(m), 4.70(s), 5.29(s), 7.53(d) and 8.24(d) ppm.

EXAMPLE 29

Following the procedure of the foregoing Examples, the following substituted azetidinones useful in the preparation of the compound of the present invention are obtained when the suggested substitution of reagents is made.

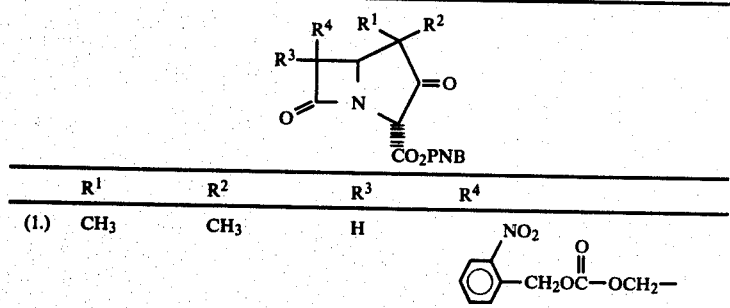

| | R$^1$ | R$^2$ | R$^3$ | R$^4$ |
|---|---|---|---|---|
| (1.) | CH$_3$ | CH$_3$ | H | 2-NO$_2$-C$_6$H$_4$-CH$_2$OC(O)-OCH$_2$- |

-continued

|     | R⁴ | R¹ | R² |
|-----|----|----|----|
|     | R³ |    |    |

Structure: β-lactam fused with substituted pyrrolidinone bearing CO₂PNB group.

| # | R¹ | R² | R³ | R⁴ |
|---|-----|-----|-----|-----|
| (2.) | CH₃ | Et | H | CH₃ |
| (3.) | CH₃ | cyclopropyl | H | C₆H₅C(=O) |

| # | R¹ | R² | R⁶ | R⁷ |
|---|-----|-----|-----|-----|
| (4.) | CH₃ | PhCH₂ | H | CH₃C(=O) |
| (5.) | CH₃ | (CH₃)₂CH | H | (CH₃)₂C(OH) |
| (6.) | CH₃ | Ph | H | CH(CH₃)N₃ |
| (7.) | CH₃ | CH₃CH₂CH₂ | CH₃ | CH(CH₃)OCO₂CH₂-(2-NO₂-C₆H₄) |
| (8.) | Et | Et | CH₃CH₂ | CH(Et)OCO₂CH₂-(3-NO₂-C₆H₄) |
| (9.) | CH₃ | H | CH₃ | CH₃C(=O) |
| (10.) | Et | CH₃ | H | CH(CH₃)OCO₂CH₂-(2-NO₂-C₆H₄) |
| (11.) | Et | Et | CH₃ | CH(CH₃)OCO₂CH₂-(2-NO₂-C₆H₄) |
| (12.) | cyclopropyl | CH₃ | CH₃ | CH(Et)OCO₂CH₂-(2-NO₂-C₆H₄) |
| (13.) | CH₃ | CH₃ | H | CH(CH₂—)(CH₂)OCO₂CH₂-(2-NO₂-C₆H₄) |
| (14.) | CH₃ | Et | H | CH(iPr)OCH₂SCH₃ |
| (15.) | H | cyclopropyl | H | CH(Ph)OCO₂CO₂CH₂-(2-NO₂-C₆H₄) |

-continued

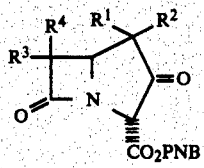

| | R¹ | R² | R³ | R⁴ |
|---|---|---|---|---|
| (16.) | CH(CH₃)₂ | CH₃ | H | Ph— |
| (17.) | CH₃ | CH₃ | H | 4-pyridyl |
| (18.) | CH₃ | H | H | 4-pyridyl |
| (19.) | CH₃ | Et | H | $-CH(CH_3)SCO_2CH_2$-(2-nitrophenyl) |
| (20.) | R¹ + R² = spirocyclopropyl | | H | $OCO_2PNB$ on CH(CH₃)₂ |
| (21.) | CH₂CH₂Br | CH₃ | H | $OCO_2PNB$ on CH(CH₃)₂ |

EXAMPLE 30

Following the foregoing text and Examples, the following species (I) are obtained when the β-lactams of Example 20 are carried through the standard procedure (Examples 10–14) to the corresponding bicyclic keto ester, followed by establishment of the thio side chain of choice and deblocking (Examples 16 and 17).

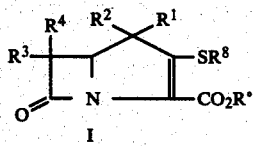

I

| Compound | R¹ | R² | R³ | R⁴ | R* | R⁸ |
|---|---|---|---|---|---|---|
| (1.) | CH₃ | —CH₃ | H | HOCH₂ | Na⁺ | cyclopropyl-NH₂ |
| (2.) | Et | —CH₃ | H | —CH₃ | Na⁺ | cyclopropyl-CH₂-NH₂ |
| (3.) | CH₃CH₂CH₂ | —CH₃ | H | PhC(=O)— | H | —(CH₂)₄NHCH(=NH)NH— |
| (4.) | cyclopropyl | H | H | CH₃C(=O)— | K⁺ | —CH₂CH(CH₃)CH₂NHC(=NH)—NH₂ |
| (5.) | cyclopropyl | —CH₃ | H | (CH₃)₂C(OH)— | CH₂OC(=O)CCl₃ | —CH₃ |
| (6.) | PhCH₂ | CH₃ | H | CH₃CH(N₃)— | H | —C(CH₃)₂CH₂NH₂ |

-continued

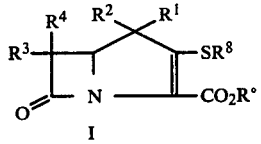

| Compound | R¹ | R² | R³ | R⁴ | R° | R⁸ |
|---|---|---|---|---|---|---|
| (7.) | Ph | CH₃ | —CH₃ | CH₃CH(OH)— | H | (CH₃)₂C(CH₃)CH₂NH₂ (neopentyl-amine type) |
| (8.) | CH₃ | CH₃ | CH₃CH₂— | HOCH₂— | —CH₂—C₆H₄—+ | —C₂H₅ |
| (9.) | (CH₃)₂CH— | CH₃ | CH₃ | CH₃C(O)— | H | —CF₂CH₂NH₂ |
| (10.) | C₄H₉ | —CH₂CH₂NH₂ | H | φCH₂CH(OH)— | H | —Ph |
| (11.) | Et | CH₃CH₂ | CH₃ | CH₃CH(OH)— | H | —C₆H₄—CH₂NH₂ |
| (12.) | CH₃ | cyclopropyl | CH₃ | HOCH₂— | Na⁺ | CH₃ |
| (13.) | cyclohexyl | CH₃ | H | CH₃CH(OH)CH₂— | (C₂H₅)₄N⁺ | CH₂NH₂ |
| (14.) | C₆H₄CH₂NH₂ | CH₃ | H | CH₃CH(OCH₂SCH₃)— | H | —CH₂-cyclopropyl-CH₂NH₂ |
| (15.) | Ph | CH₃ | H | C₆H₅CH(OH)— | H | CH₂CH₂C(=NH)—NH₂ |
| (16.) | CH₃ | CH₃CH(CH₃)— | H | C₆H₅— | H | (CH₃)₂CHCH₂NH |
| (17.) | CH₃ | CH₃ | H | pyridyl | Na⁺ | CH(CO₂H)(NH₂)CH₂— |
| (18.) | Et | CH₃ | H | methylpyridyl | H | pyridyl |
| (19.) | CH₃ | CH₃ | H | CH₃CH(SH)— | K⁺ | —CH₃ |
| (20.) | R¹ + R² = spirocyclopropyl | | H | CH₃CH(OH)— | Na | —CH₂CH₂NHC(=NH)—H |

What is claimed is:

1. A compound having the structure:

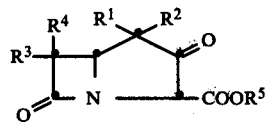

wherein R¹, R², R³ and R⁴ are independently selected from the group consisting of hydrogen, (R¹ and R² are not both hydrogen), substituted and unsubstituted: alkyl, alkenyl, and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; spirocycloalkyl having 3-6 carbon atoms; phenyl; aralkyl, aralkenyl, and aralkynyl wherein the aryl moiety is phenyl and the alkyl chain has 1-6 carbon atoms; wherein the substituent or substituents relative to the above-named radicals are selected from the group consisting of: amino, mono-, di-, and trialkylamino, hydroxyl, alkoxyl, mercapto, alkylthio, phenylthio, sulfamoyl, amidino, guanidino, nitro, chloro, bromo, fluoro, iodo, cyano, and carboxy; and wherein the alkyl moieties of the above-recited substituents have 1–6 carbon atoms; $R^5$ is hydrogen, salt cation, a pharmaceutically acceptable ester moiety or a removable blocking group.

2. A compound according to claim 1 wherein $R^1$ and $R^2$ are selected from hydrogen, alkyl, cycloalkyl, spirocycloalkyl, benzyl or phenyl; and $R^3$ is H or methyl and $R^4$ is alkyl, phenyl, aralkyl or hydroxyl-substituted: alkyl, phenyl or aralkyl.

3. A compound according to claim 2 wherein $R^1$ and $R^2$ are selected from hydrogen, spirocyclopropyl, cyclopropyl, methyl, ethyl, isopropyl, t-butyl, or phenyl and $R^4$ is 1-hydroxyethyl, methyl or hydroxymethyl.

4. A compound according to claim 3 wherein $R^4$ is $CH_3CH(OH)$, and $R^5$ is H.

5. A compound according to claim 3 wherein $R^1$ is hydrogen, $R^2$ is selected from methyl, ethyl, isopropyl, t-butyl, phenyl or cyclopropyl, spirocyclopropyl, $R^4$ is 1-hydroxyethyl, methyl or hydroxymethyl.

6. A compound according to claim 3 wherein $R^1$ is methyl and $R^2$ is hydrogen; $R^4$ is $CH_3CH(OH)$ and $R^3$ is hydrogen.

7. A compound according to claim 3 wherein $R^1$ and $R^2$ are methyl; $R^4$ is $CH_3CH(OH)$ and $R^3$ is hydrogen.

* * * * *